US012636021B2

(12) United States Patent

Shuman et al.

(10) Patent No.: US 12,636,021 B2

(45) Date of Patent: May 26, 2026

(54) RF BIPOLAR STEAM GENERATION ABLATION DEVICE

(71) Applicant: GYRUS ACMI, INC., Westborough, MA (US)

(72) Inventors: Brandon J. Shuman, Kirkland, WA (US); Peter A. Lambe, Redmond, WA (US)

(73) Assignee: Gyrus ACMI, Inc., Westborough, MA (US)

( * ) Notice: Subject to any disclaimer, the term of this patent is extended or adjusted under 35 U.S.C. 154(b) by 1066 days.

(21) Appl. No.: 15/934,844

(22) Filed: Mar. 23, 2018

(65) Prior Publication Data

US 2019/0290300 A1 Sep. 26, 2019

(51) Int. Cl.
*A61B 17/22* (2006.01)
*A61B 17/32* (2006.01)
(Continued)

(52) U.S. Cl.
CPC ...... *A61B 17/22* (2013.01); *A61B 17/320068* (2013.01); *A61B 18/082* (2013.01);
(Continued)

(58) Field of Classification Search
CPC ......... A61B 17/22; A61B 90/13; A61B 19/11; A61B 18/082; A61B 18/1492;
(Continued)

(56) References Cited

U.S. PATENT DOCUMENTS 5,843,079 A * 12/1998 Suslov ................. A61B 18/042
606/43
6,475,215 B1 * 11/2002 Tanrisever ........... A61B 18/042
606/32
(Continued)

OTHER PUBLICATIONS

"U.S. Appl. No. 15/934,844, Response filed Nov. 24, 2021 to Non Final Office Action mailed Aug. 27, 2021", 16 pgs.

*Primary Examiner* — Linda C Dvorak
(74) *Attorney, Agent, or Firm* — Schwegman Lundberg & Woessner, P.A.

(57) ABSTRACT

Disclosed embodiments include apparatuses, systems, and methods for vaporizing a conductive fluid at or adjacent a reference point. In an illustrative embodiment, an apparatus includes a primary electrode extending to a first distal end positionable adjacent to a reference point and having a first proximal end selectively couplable with a first pole of a power source. The primary electrode defines a lumen therein and defines at least one opening to the lumen within a distal range adjacent the first distal end. A secondary electrode extends through the lumen of the primary electrode and has a second distal end extending into the distal range and a second proximal end selectively couplable with a second pole of the power source. The secondary electrode is electrically insulated from the primary electrode except within the distal range, where a conductive fluid is receivable within the distal range so as to be in electrical contact with the primary electrode and the secondary electrode. The conductive fluid is vaporizable at the distal range responsive (Continued)

to application of power across the first pole and the second pole of the power source and vaporized conductive fluid is expellable through the at least one opening.

14 Claims, 12 Drawing Sheets

(51) Int. Cl.

| | |
|---|---|
| *A61B 18/00* | (2006.01) |
| *A61B 18/08* | (2006.01) |
| *A61B 18/14* | (2006.01) |
| *A61B 90/13* | (2016.01) |
| *A61B 18/04* | (2006.01) |

(52) U.S. Cl.
CPC .......... *A61B 18/1492* (2013.01); *A61B 90/13* (2016.02); *A61B 2018/00541* (2013.01); *A61B 2018/00577* (2013.01); *A61B 2018/00982* (2013.01); *A61B 2018/048* (2013.01); *A61B 2018/1425* (2013.01)

(58) Field of Classification Search
CPC ........ A61B 18/042; A61B 2018/00577; A61B 2018/00625; A61B 2018/1425; A61B 2018/1477

See application file for complete search history.

(56) References Cited

U.S. PATENT DOCUMENTS

| | | | | |
|---|---|---|---|---|
| 9,345,532 | B2 | 5/2016 | Laufer | |
| 2001/0032001 | A1* | 10/2001 | Ricart ................ | A61B 18/1482 607/99 |
| 2007/0029292 | A1* | 2/2007 | Suslov ..................... | H05H 1/28 219/121.59 |
| 2010/0041949 | A1* | 2/2010 | Tolkowsky ...... | A61B 17/12104 600/117 |
| 2011/0077635 | A1* | 3/2011 | Bonn ................. | A61B 18/1815 606/33 |
| 2012/0101494 | A1* | 4/2012 | Cadouri .............. | A61B 18/148 606/41 |
| 2012/0265190 | A1* | 10/2012 | Curley .............. | A61B 18/1477 606/28 |
| 2014/0066917 | A1* | 3/2014 | Cosman, Jr. .......... | A61B 18/18 606/33 |
| 2016/0262821 | A1 | 9/2016 | Azamian et al. | |

* cited by examiner

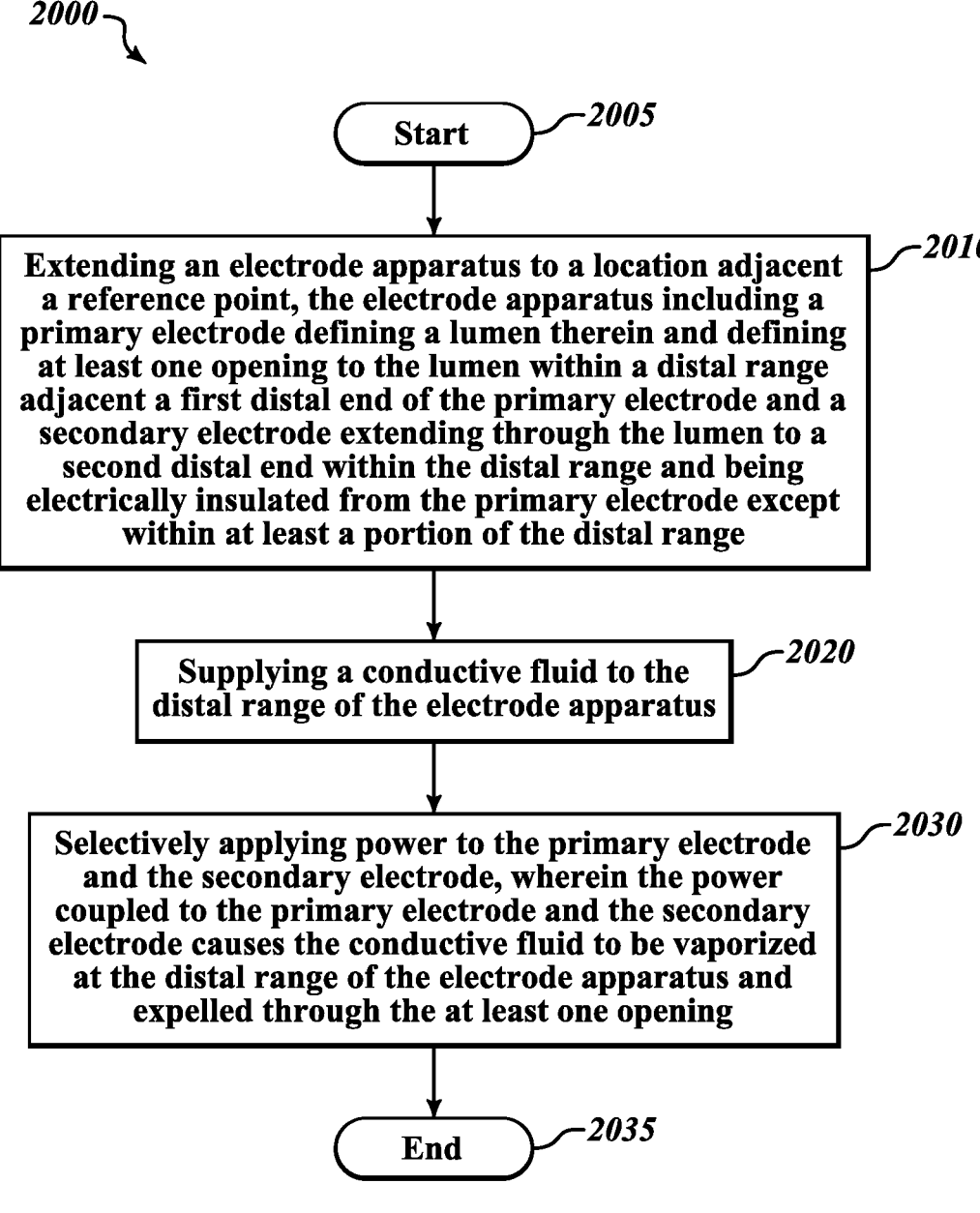

*2000*

Start — *2005*

Extending an electrode apparatus to a location adjacent a reference point, the electrode apparatus including a primary electrode defining a lumen therein and defining at least one opening to the lumen within a distal range adjacent a first distal end of the primary electrode and a secondary electrode extending through the lumen to a second distal end within the distal range and being electrically insulated from the primary electrode except within at least a portion of the distal range — *2010*

Supplying a conductive fluid to the distal range of the electrode apparatus — *2020*

Selectively applying power to the primary electrode and the secondary electrode, wherein the power coupled to the primary electrode and the secondary electrode causes the conductive fluid to be vaporized at the distal range of the electrode apparatus and expelled through the at least one opening — *2030*

End — *2035*

*FIG.20*

RF BIPOLAR STEAM GENERATION ABLATION DEVICE

FIELD

The present disclosure relates to vaporizing a conductive fluid at a reference point.

BACKGROUND

The statements in this section merely provide background information related to the present disclosure and may not constitute prior art.

The ability to access tissues within a patient's body without invasive surgery allows for ever-improving types of analysis, diagnosis, and treatment with reduced pain, reduced recovery time, and a reduced risk of complications. By way of two examples, endoscopic imaging and catherization treatments have enabled evaluation and treatment of numerous internal lesions without invasive surgery.

Electrosurgical techniques also provide for minimally invasive therapies by selectively applying electrical power to selected tissues. Electrosurgical techniques involve extending one or more electrodes through an orifice or a small incision to a desired location within a body, then applying electric power, such as in the form or a radio frequency ("RF") electric current, to the electrodes to coagulate and/or ablate tissue at that location. Monopolar electrosurgical instruments only entail use of one electrode that interacts with a neutral electrode, which is connected to the body of a patient. A bipolar electrosurgical instrument typically includes a user interface used for positioning two electrodes, which may include a distal electrode and a proximal electrode.

Positioning two electrodes at the desired location is an important part of bipolar electrosurgical treatments to treat patients. However, moving each of the two electrodes to positions at opposite sides of the desired location to ablate or otherwise treat tissue between them may present a challenge for the medical personnel directing the treatment.

SUMMARY

Disclosed embodiments include apparatuses, systems, and methods for vaporizing a conductive fluid at or adjacent a reference point using two bipolar electrodes.

In an illustrative embodiment, an apparatus includes a primary electrode extending to a first distal end positionable adjacent to a reference point and having a first proximal end selectively couplable with a first pole of a power source. The primary electrode defines a lumen therein and defines at least one opening to the lumen within a distal range adjacent the first distal end. A secondary electrode extends through the lumen of the primary electrode and has a second distal end extending into the distal range and a second proximal end selectively couplable with a second pole of the power source. The secondary electrode is electrically insulated from the primary electrode except within the distal range, where a conductive fluid is receivable within the distal range so as to be in electrical contact with the primary electrode and the secondary electrode. The conductive fluid is vaporizable at the distal range responsive to application of power across the first pole and the second pole of the power source and vaporized conductive fluid is expellable through the at least one opening.

In another illustrative embodiment, a system includes a power source configured to selectively power between a first pole and a second pole. The system includes a conductive fluid source. The system also includes a primary electrode extending to a first distal end positionable adjacent to a reference point and having a first proximal end selectively couplable with a first pole of a power source. The primary electrode defines a lumen therein and defines at least one opening to the lumen within a distal range adjacent the first distal end. The lumen is configured to receive conductive fluid from the conductive fluid source. A secondary electrode extends through the lumen of the primary electrode and has a second distal end extending into the distal range and a second proximal end selectively couplable with a second pole of the power source. The secondary electrode is electrically insulated from the primary electrode except within the distal range, where a conductive fluid is receivable within the distal range so as to be in electrical contact with the primary electrode and the secondary electrode. The conductive fluid is vaporizable at the distal range responsive to application of power across the first pole and the second pole of the power source and vaporized conductive fluid is expellable through the at least one opening.

In a further illustrative embodiment, a method is provided for operating an electrode apparatus. An electrode apparatus is extended to a location adjacent a reference point. The electrode apparatus includes a primary electrode defining a lumen therein and defining at least one opening to the lumen within a distal range adjacent a first distal end of the primary electrode. A secondary electrode extends through the lumen to a second distal end within the distal range and is electrically insulated from the primary electrode except within at least a portion of the distal range. A conductive fluid is supplied to the distal range of the electrode apparatus. Power is selectively applied to the primary electrode and the secondary electrode, such that the power coupled to the primary electrode and the secondary electrode causes the conductive fluid to be vaporized at the distal range of the electrode apparatus and expelled through the at least one opening.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, with emphasis instead being placed upon illustrating the principles of the disclosed embodiments. In the drawings.

Figure 1:
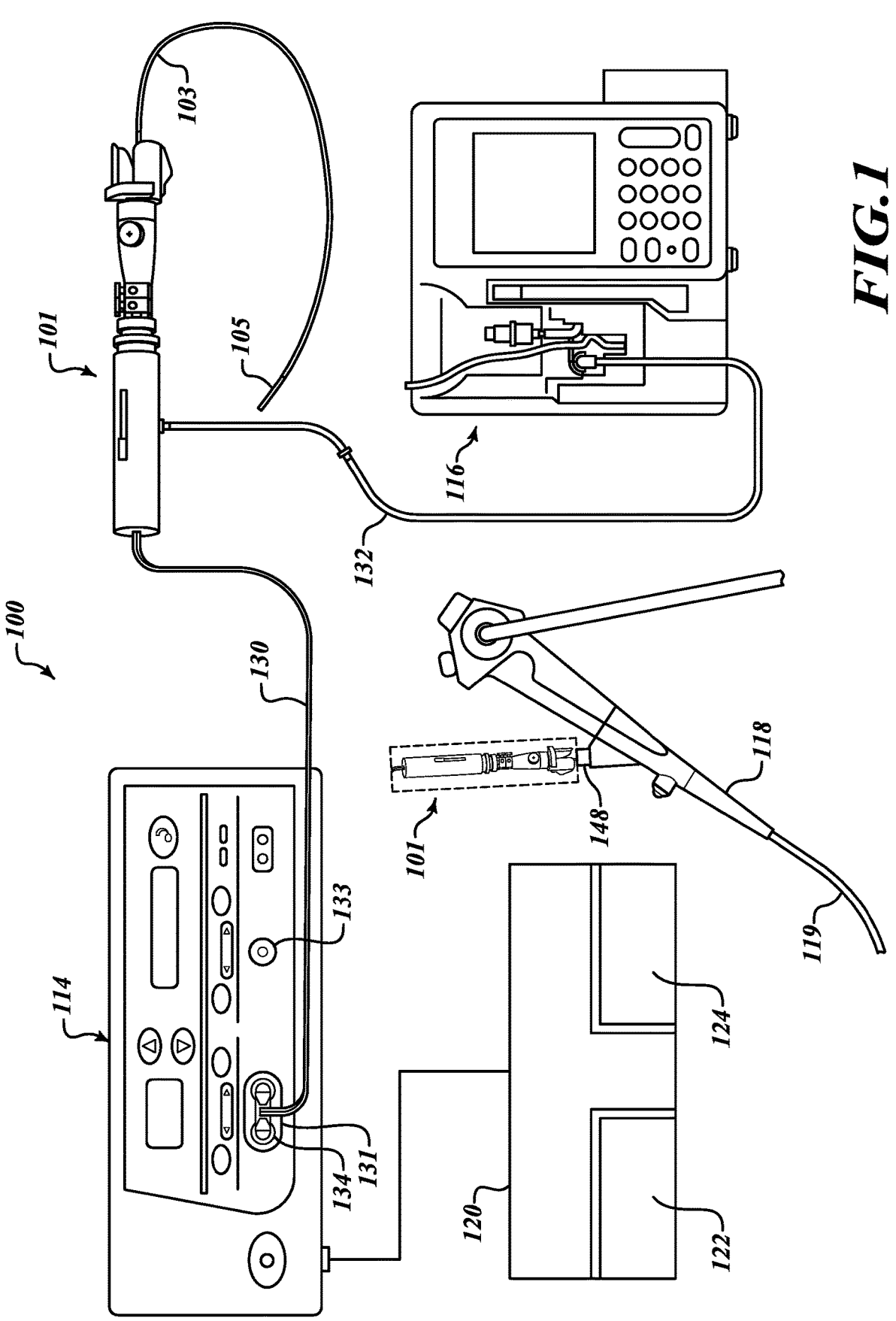
FIG. 1 is a block diagram in partial schematic form of an illustrative system for treating tissue using embodiments according to the present disclosure.
Figure 2B:
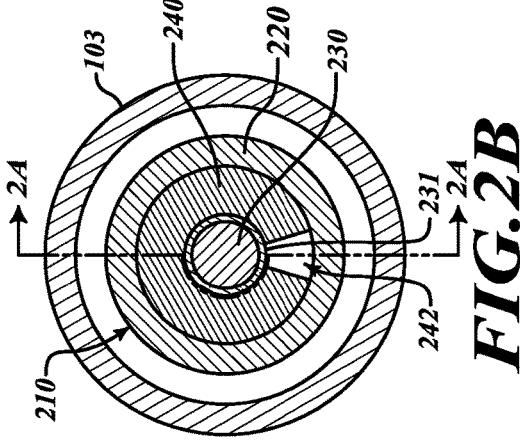
FIGS. 2B and 3B are cross sectional views of the electrode apparatuses of FIGS. 2A and 3A, respectively.
Figure 2A:
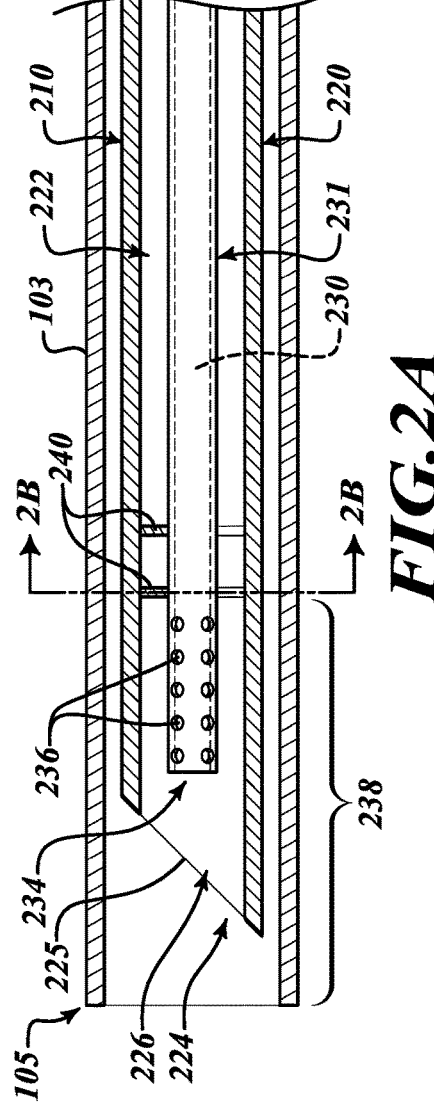
FIGS. 2A and 3A are side plan views in cutaway of embodiments of an electrode apparatus.
Figure 4A:
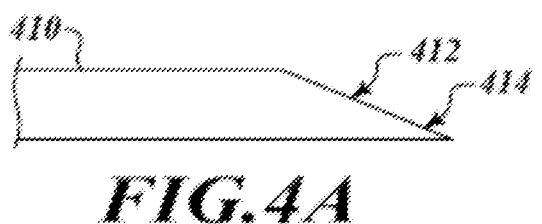
Figure 4B:
Figure 4C:
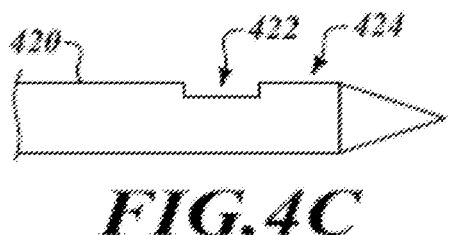
Figure 4D:
Figure 4E:
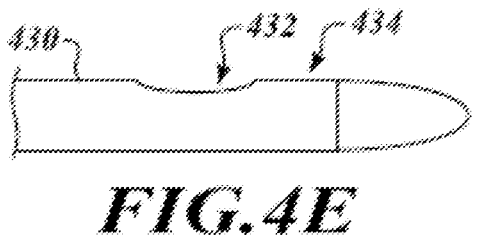
Figure 4F:
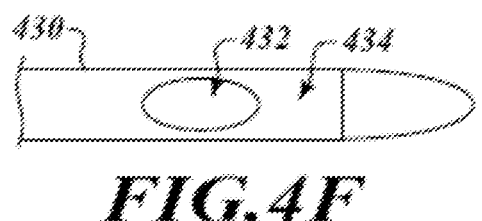
Figure 6:
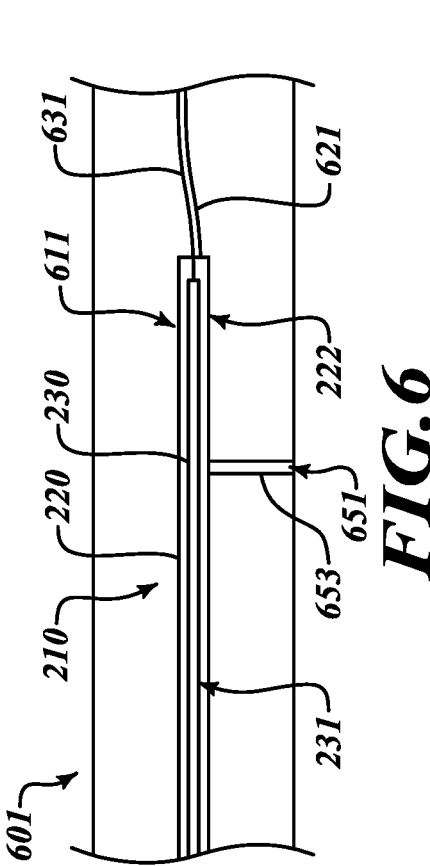
Figure 7:
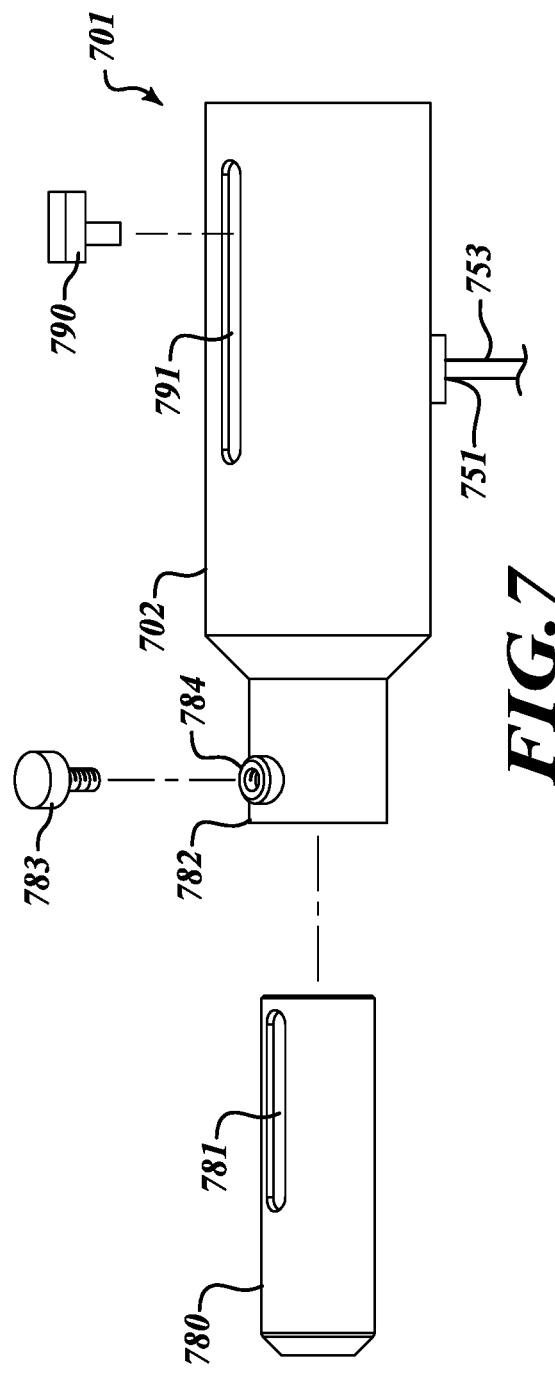
Figure 8A:
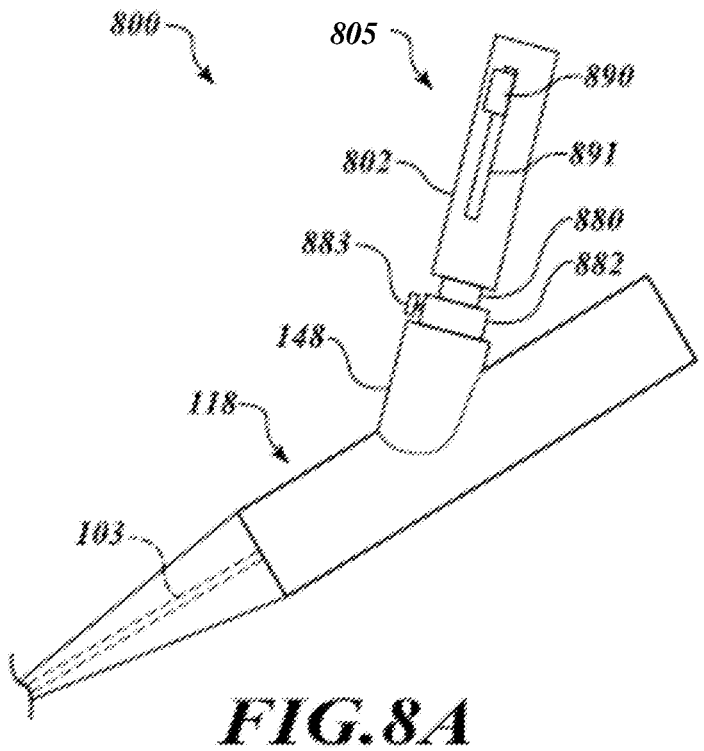
Figure 8B:
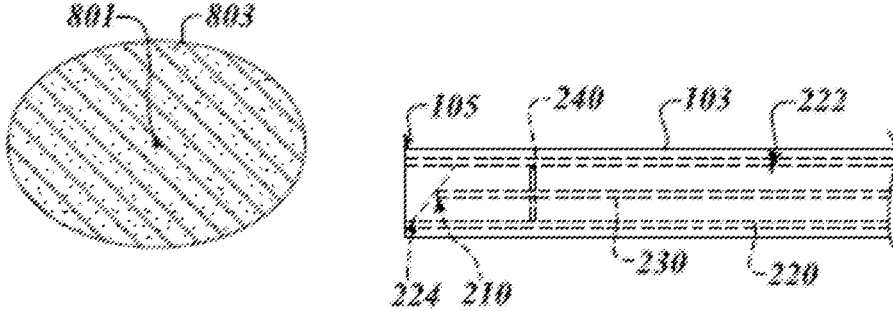
Figure 9A:
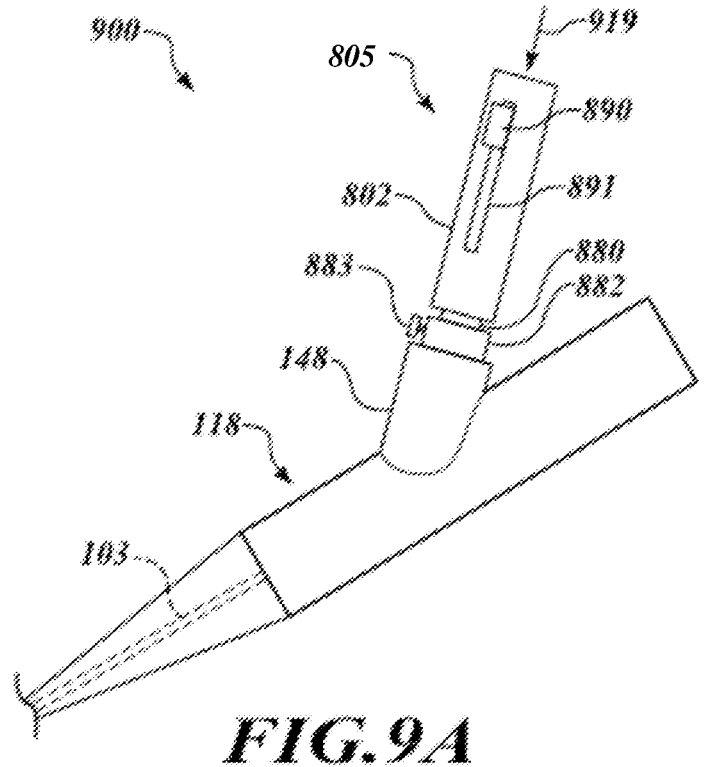
Figure 9B:
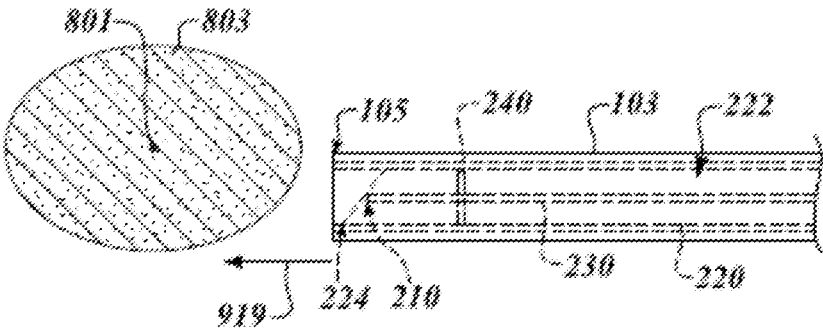
Figure 10A:
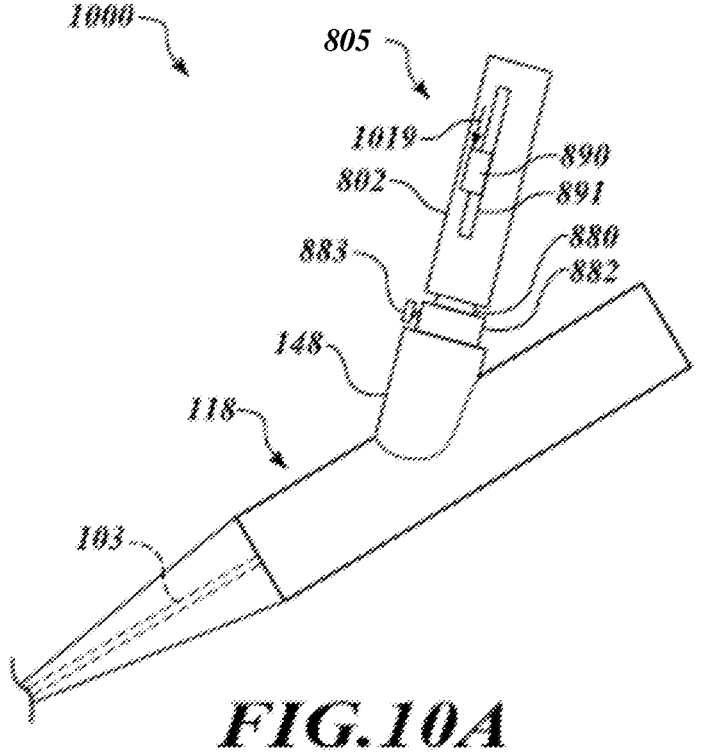
Figure 10B:
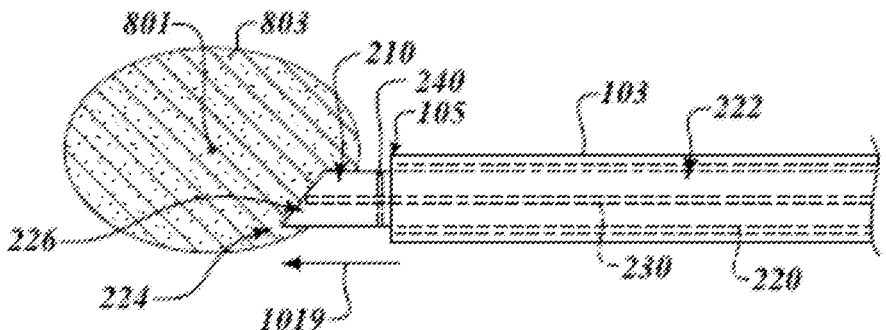
Figures 11, 12:
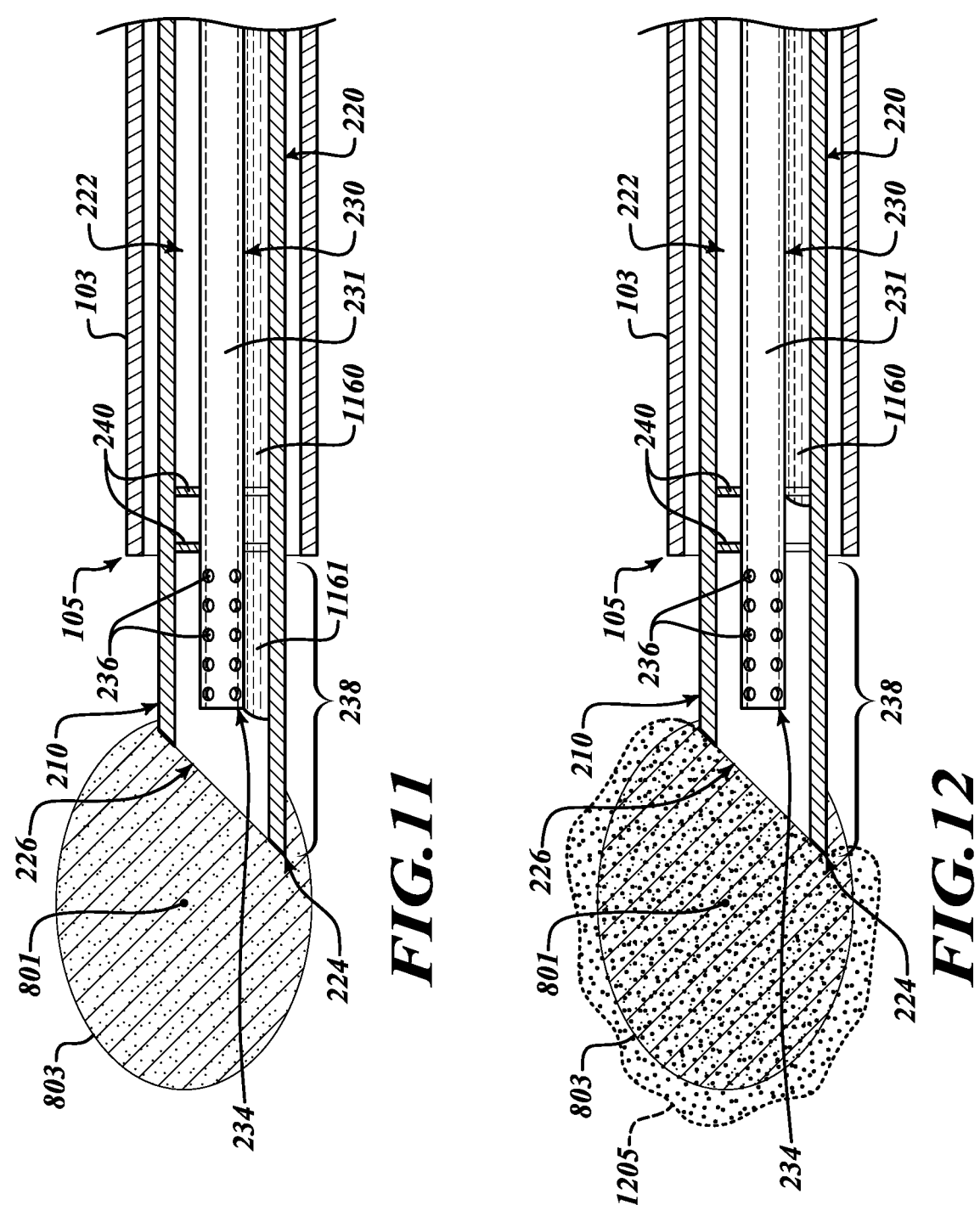
Figure 17:
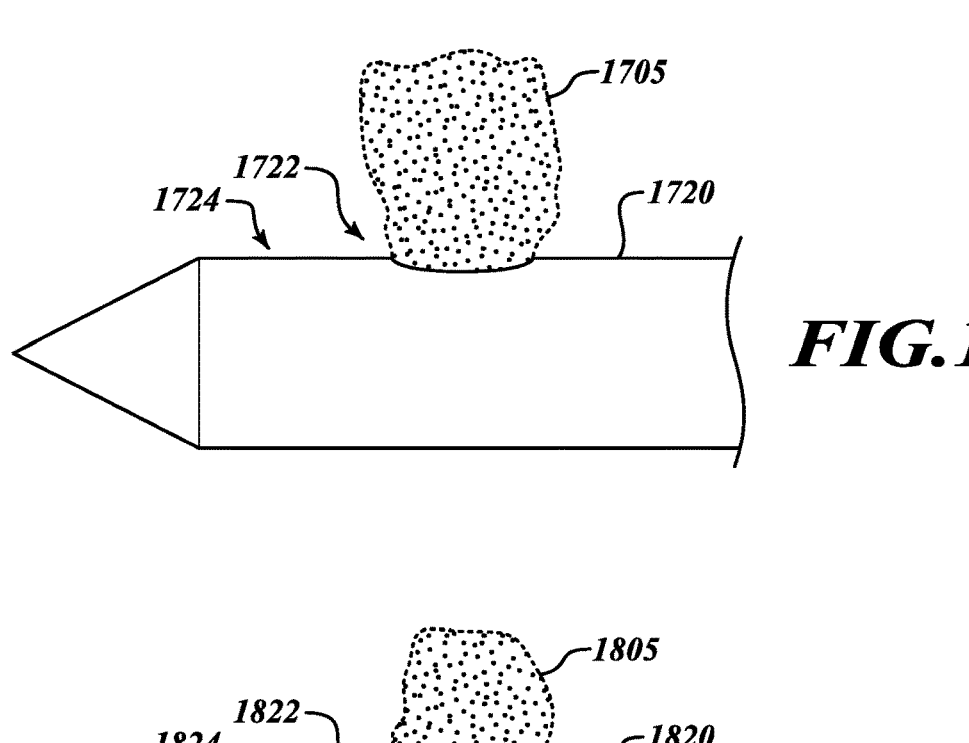
Figure 18:
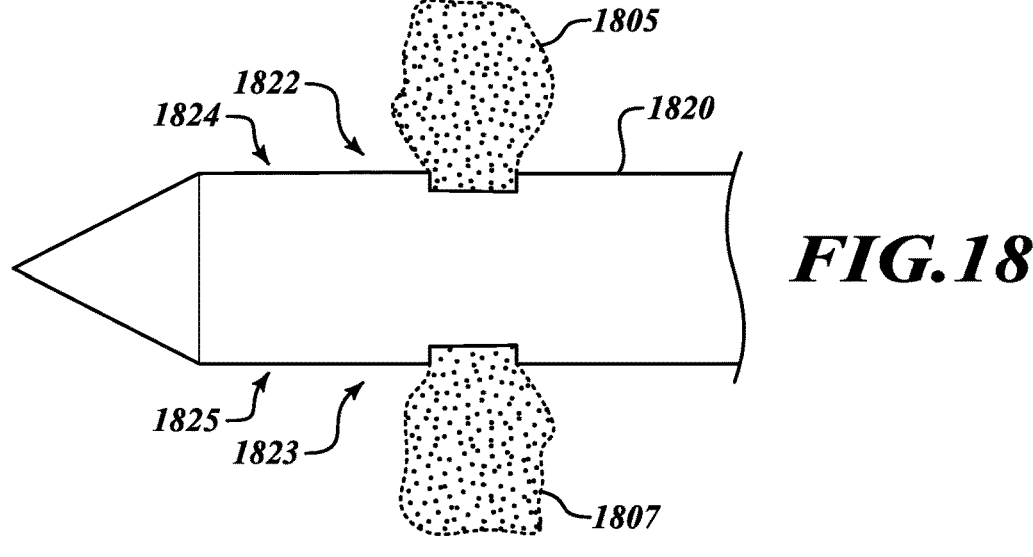
Figure 19:
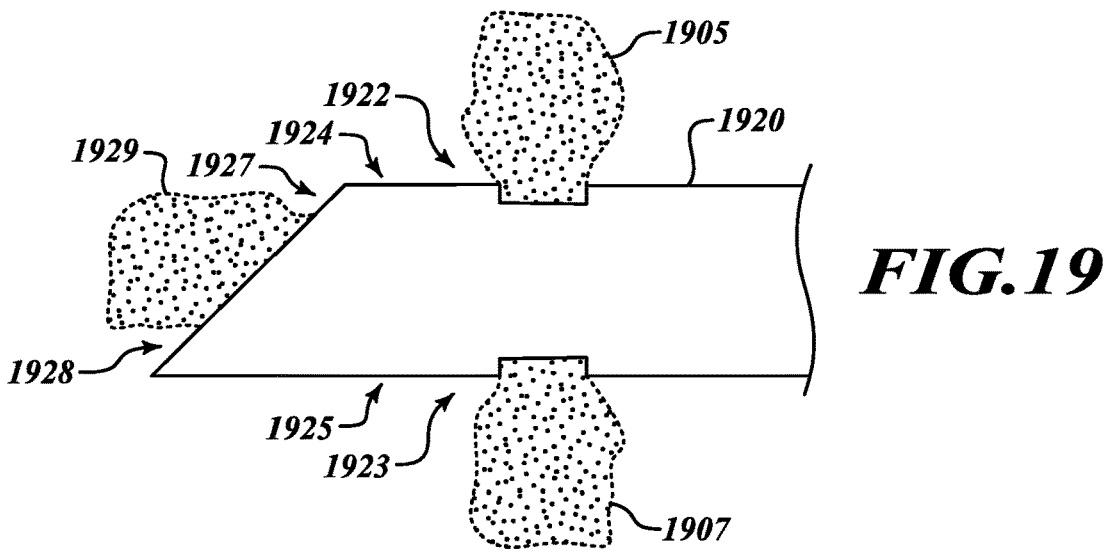

FIGS. 4A, 4C, and 4E are side plan views of primary electrodes of the electrode apparatus having single openings of different types;

FIGS. 4B, 4D, and 4F are top plan views of the primary electrodes of FIGS. 4A, 4C, and 4E;

FIGS. 5A-5D are side plan views of primary electrodes of the electrode apparatus having multiple openings;

FIG. 6 is a side plan view in partial cutaway of the user interface of FIG. 1;

FIG. 7 is an exploded view of the user interface of FIG. 1;

FIGS. 8A and 9A illustrate operation of a sheath actuator;

FIGS. 8B and 9B illustrate positioning of a distal end of a sheath containing the electrode apparatus in proximity to a reference point corresponding with operation of the sheath actuator as shown in FIGS. 8A and 9A, respectively;

FIG. 10A illustrates operation of an electrode actuator of the user interface of FIGS. 8A and 9A to extend the electrode apparatus to a position at or adjacent to the reference point;

FIG. 10B illustrates positioning of extending the electrode apparatus at or adjacent the reference point corresponding with operation of the electrode actuator as shown in FIG. 10A;

FIGS. 11 and 12 are side plan views in cutaway that illustrate operation of the electrode apparatus of FIGS. 2A and 2B;

FIGS. 13-16 are side plan views in cutaway that illustrate operation of another embodiment of the electrode apparatus;

FIGS. 17-19 are side plan views of other illustrative embodiments of the electrode apparatus having different configurations of openings through which vaporized conductive fluid is expelled; and FIG. 20 is a flow diagram of an illustrative method of operating an electrode apparatus.

DETAILED DESCRIPTION

The following description is merely illustrative in nature and is not intended to limit the present disclosure, application, or uses. It will be noted that the first digit of three-digit reference numbers and the first two digits of four-digit reference numbers correspond to the first digit of one-digit figure numbers and the first two-digits of the figure numbers, respectively, in which the element first appears.

The following description explains, by way of illustration only and not of limitation, various embodiments of user interfaces to position electrodes for electrosurgical apparatuses, as well as systems including such user interfaces and methods of using the same. As will be described in detail below, electrosurgical techniques position first and second electrodes at a location adjacent a reference point where electrical treatment, such as ablative treatment, is to be applied. For a specific example, the user interfaces and methods of their use may be used for ablating and/or coagulating tissue, removing lesions, and for performing other medical procedures within the lung.

It will be appreciated that various embodiments of user interfaces described herein are used for vaporizing a conductive fluid at or adjacent to a reference point, for example, to ablate tissue at or adjacent to the reference point. As will be described below, various embodiments of an electrode apparatus and a system are used to position the electrode apparatus at a location adjacent to the reference point, to supply conductive fluid to a distal range of the electrode apparatus where two electrodes will come in contact with the conductive fluid, and to selectively apply power to the two electrodes to vaporize the conductive fluid to effect treatment.

Referring to FIG. 1, in various embodiments an illustrative system 100 is provided for ablating or otherwise treating tissue adjacent to a reference point in an anatomical region of a patient (not shown in FIG. 1). The system 100 may be a bipolar radio frequency (RF) system, as desired, for treating tissue in a patient. Specifically, the system 100 may be employed for coagulation and/or ablation of soft tissue during percutaneous and/or endoscopic procedures, including bronchoscopic or endoscopic surgical procedures, such as, for example, partial and/or complete ablation of cancerous and/or noncancerous organ lesions. As will be further described, in various embodiments the tissue is treated by positioning an electrode apparatus proximate the tissue to be treated, supplying a quantity of conductive fluid to a distal range of the electrode apparatus at or near the reference point, and applying electrical power to the electrode apparatus to vaporize the conductive fluid through the tissue at or adjacent to the reference point. As a result, tissue at or adjacent to the reference point may be ablated, for example, thereby helping to eliminate cancerous and/or noncancerous organ lesions.

In some embodiments, the system 100 includes a user interface 101, an electrosurgical radio frequency (RF) generator operating as a switchable power source 114, a conductive fluid source 116, such as an infusion pump, and an electrosurgical instrument or apparatus, such as, without limitation, a bronchoscope 118. It will be appreciated that the electrosurgical instrument or apparatus may also include an endoscope or any other electrosurgical instrument as desired for a particular application. The bronchoscope 118 may be configured to receive the user interface 101 at a port 148 to enable the user interface 101 to manipulate electrodes at the reference point via the bronchoscope 118.

The user interface 101 electrically communicates with the switchable power source 114 though an electrical conductor 130. In some embodiments, the electrical conductor 130 is connected to an outlet 131 when the system is operated in a bipolar mode. The electrical conductor 130 may be coupled with the outlet 131 using an electrical connector 134 configured to electrically engage the outlet 131. The user interface 101 is further connected to the conductive fluid source 116 with a tube 132 that facilitates the flow of liquid, for example saline solution or another conductive fluid, from the conductive fluid source 116 to the user interface 101. A flow of conductive fluid from the conductive fluid source 116 may be controlled via a switch, such as a switch on the conductive fluid source 116 or a remote switch (not shown) such as a hand switch or a foot switch.

The switchable power source 114 can be operated with the use of a foot operated unit 120 electrically connected to the switchable power source 114. The foot operated unit 120 may include, for example, a pedal 122 that instructs the switchable power source 114 to apply electrical power to electrode(s) (described below) to cut and/or ablate tissue and a pedal 124 that instructs the generator 114 to apply a lower quantity of electrical power to the electrode(s) to coagulate tissue.

In various embodiments the bronchoscope 118 includes an insertion tube 119 that permits insertion of a sheath 103 into a body (not shown). A distal end 105 of the sheath 103 is delivered to a location near the tissue to be treated at the reference point. The sheath 103 contains and conveys the electrodes (not shown) to a desired treatment location. Positioning of the distal end 105 of the sheath 103 and the distal ends of the electrodes (not shown in FIG. 1) may be controlled by the user interface 101 received by the bronchoscope 118 at a port 148, as further described below with reference to FIGS. 8A, 9A, and 10A.

Referring to FIG. 2A, in various embodiments an electrode apparatus 210 is positioned within the distal end 105 of the sheath 103. The electrode apparatus 210 includes a primary electrode 220 and a secondary electrode 230. In some embodiments, the primary electrode 220 is a hollow, needle-shaped structure. The primary electrode 220 defines a lumen 222, an interior annular passage. In some embodiments, the lumen 222 extends the length of the electrode apparatus 210 from a first proximal end (not shown in FIG. 2A) at the user interface 101 (FIG. 1) to a tip 225 of the primary electrode 220 at a first distal end 224 of the primary electrode 220. The secondary electrode 230 extends within the lumen 222. In some embodiments, the secondary electrode 230 extends the length of the electrode apparatus 210 from a second proximal end (not shown in FIG. 2A) at the user interface 101 to a second distal end 234 of the secondary electrode 230 into a distal range 238 adjacent the first distal end 224 of the primary electrode 220. The connection of the proximal ends of the primary electrode 220 and the secondary electrode 230 is further described below with reference to FIG. 6.

The secondary electrode 230 is electrically isolated from the primary electrode 220 until the two are electrically connected by a conductive fluid (not shown in FIG. 2A) as further described below. In some embodiments, the secondary electrode 230 is coated with electrical insulation 231 that electrically isolates the secondary electrode 230 from the primary electrode 220 through nearly the entire length of the electrode apparatus 210. The only portion of the electrode apparatus 210 in which the secondary electrode 230 is not electrically isolated from the primary electrode 220 is in the distal range 238 adjacent to the first distal end 224 of the primary electrode 220 and the second distal end 234 of the secondary electrode 230. In some embodiments, as shown in FIG. 2A, openings 236 are formed in the electrical insulation 231 covering the secondary electrode 230 in the distal range 238. The openings 236 may include laser-drilled holes in the electrical insulation 231.

In some embodiments, the secondary electrode 230 may also be physically isolated from the primary electrode by one or more separators 240 that space the secondary electrode 230 from the primary electrode 220 within the lumen 222. Referring to FIG. 2B and according to various embodiments, a cross-sectional view of the electrode apparatus 210 within the sheath 103 taken along axis 2B of FIG. 2A shows the separator 240. In such embodiments, the separator 240 extends from the electrical insulation 231 of the secondary electrode 230 across the lumen 222 (FIG. 2A) to the primary electrode 230 except at one or more fluid openings 242 along the circumference of the separator 240. As described further below, in some embodiments the conductive fluid (not shown in FIGS. 2A and 2B) is conveyed to the distal range 238 of the electrode apparatus 210 through the lumen 222 from at or near the proximal ends (not shown in FIGS. 2A and 2B) of the primary electrode 220 and the secondary electrode 230 to the distal range 238. If more than one separator 240 is used, each of the separators 240 may include the fluid openings 242 to enable the conductive fluid to pass through the lumen 222 into the distal range 238 of the electrode apparatus 210.

Referring again to FIG. 2A, the primary electrode 220 also includes at least one opening 226 to the lumen 222 defined by the primary electrode 220 at the tip 225 of the primary electrode 220. As further described below with reference to FIGS. 4A-4F and 5A-5D, openings to the lumen 222 may be formed other than at the tip 225 or in addition to the opening 226 at the tip 225. Also, as further described in detail below with reference to FIGS. 12 and 16, when the conductive fluid (not shown in FIG. 2A) is vaporized in the distal range 238 by the application of electrical power across the primary electrode 220 and the secondary electrode 230, vaporized conductive fluid exits the lumen 222 via the at least one opening 226. Vaporized conductive fluid exiting the at least one opening 226 may contact a lesion or other tissue at or adjacent to the at least one opening 226 to effect a treatment of the lesions or other tissue.

Figure 3B:
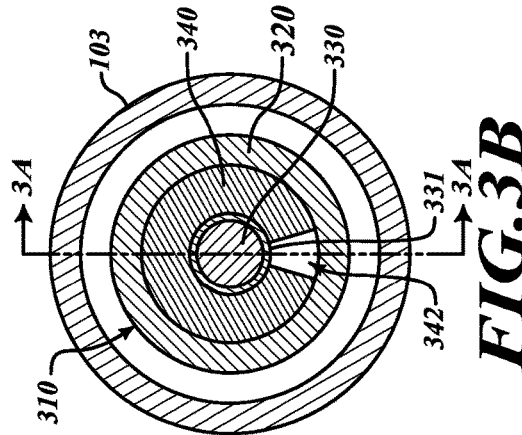
Figure 3A:
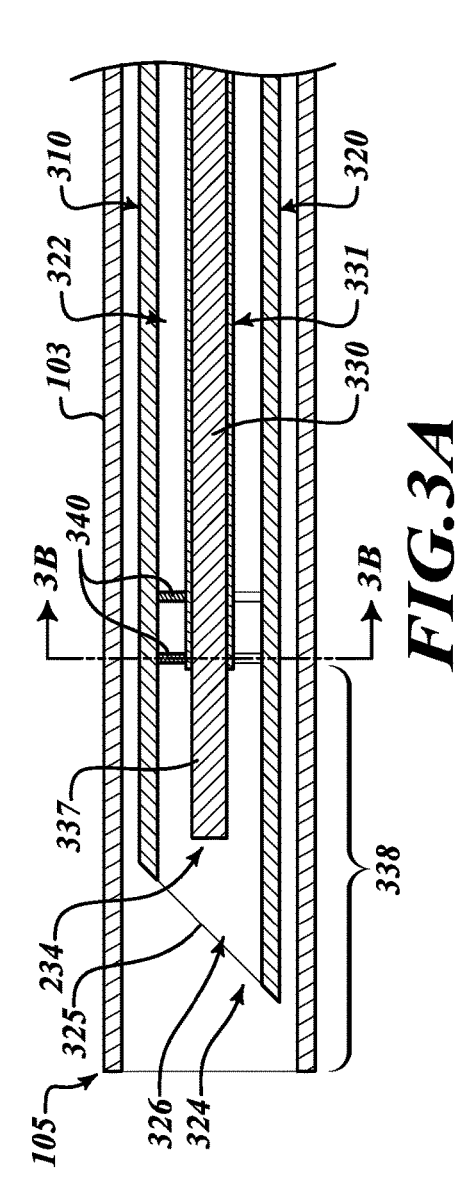

Referring to FIG. 3A, in some other embodiments the electrode apparatus 310 includes a different configuration of the secondary electrode 330 in the distal range 338. Most aspects of the electrode apparatus 310 are identical or similar to the electrode apparatus 210 of FIGS. 2A and 2B. The electrode apparatus 310 is positioned within the distal end 105 of the sheath 103. The electrode apparatus 310 includes a primary electrode 320 and a secondary electrode 330. In some embodiments, the primary electrode 320 is a hollow, needle-shaped structure. The primary electrode 320 defines a lumen 322 that extends the length of the electrode apparatus 310 from a first proximal end (not shown in FIG. 3A) at the user interface 101 (FIG. 1) to a tip 325 at a first distal end 324 of the primary electrode 320. The secondary electrode 330 extends within the lumen 322. In some embodiments, the secondary electrode 330 extends the length of the electrode apparatus 310 from a second proximal end (not shown in FIG. 3A) at the user interface 101 into a distal range 238 at a second distal end 334 of the secondary electrode 330. The connection of the proximal ends of the primary electrode 320 and the secondary electrode 330 is further described below with reference to FIG. 6.

The secondary electrode 330 is electrically isolated from the primary electrode 320 until the two are electrically connected by a conductive fluid (not shown in FIG. 3A) as further described below. In some embodiments, the secondary electrode 330 is coated in electrical insulation 331 that electrically isolates the secondary electrode 330 from the primary electrode 320 through nearly the entire length of the electrode apparatus 310. The only portion of the electrode apparatus 310 in which the secondary electrode 330 is not electrically isolated from the primary electrode 320 is at a bared end 337 of the secondary electrode 330 in a distal range 338 near the first distal end 324 of the primary electrode 320 and the second distal end 334 of the secondary electrode 330. In forming the bared end 337 of the secondary electrode 330, the electrical insulation 331 may be removed from the secondary electrode 330 along the bared end 337, or the electrical insulation 331 may not have been deposited on the secondary electrode 330 at the bared end 337 of the secondary electrode 330.

As in embodiments of the electrode apparatus 210 (FIGS. 2A and 2B), in various embodiments, the secondary electrode 330 may also be physically isolated from the primary electrode by one or more separators 340 that space the secondary electrode 330 from the primary electrode 320 within the lumen 322. Referring to FIG. 3B and in various embodiments, the separator 340 extends from insulation 331 covering the secondary electrode 330 to the primary electrode 320 except at one or more fluid openings 342 along the circumference of the separator 340. In other embodiments, one or more of the separators 340 may extend across the lumen 322 directly from the bared end 337 of the secondary electrode 330 to the primary electrode 320 except at the one or more fluid openings 342 along the circumference of the separator 340. As described further below, in some embodiments the conductive fluid (not shown in FIGS. 3A and 3B) is conveyed to the distal range 338 of the electrode apparatus 310 through the lumen 322 from at or near the proximal ends (not shown in FIGS. 3A and 3B) of the primary electrode 320 and the secondary electrode 330 to the distal range 338. If more than one separator 340 is used, each of the separators 340 may include the fluid openings 342 to enable the conductive fluid to pass through the lumen 322 into the distal range 338 of the electrode apparatus 310.

Referring again to FIG. 3A, and similar to the electrode apparatus 210 described with reference to FIG. 2A, the primary electrode 320 also includes at least one opening 326 to the lumen 322 defined by the primary electrode 320 at the tip 325 of the primary electrode 320. As further described below with reference to FIGS. 4A-4F and 5A-5D, openings may be formed in the lumen 322 other than at the tip 325 or in addition to the at least one opening 326 at the tip 325. Also, as further described in detail below with reference to FIGS. 12 and 16, when the conductive fluid (not shown in FIG. 3A) is vaporized at the distal ends 324 and 334 of the primary electrode 320 and the secondary electrode 330, respectively, the vaporized conductive fluid exits the lumen 322 via the at least one opening 326. The heated and vaporized fluid exiting the at least one opening 326 may contact a lesion or other tissue at or adjacent the opening 326 to effect a treatment of the lesions or other tissue.

The illustrative embodiments of FIGS. 2A and 3A show the at least one opening 226 and 326 at the tip 225 and 325 of the primary electrode 220 and 320, respectively. However, as previously mentioned, the primary electrode 220 and 320 includes one opening 226 and 326, respectively. The primary electrode 220 and 320 may include multiple openings therein. In addition, the at least one opening 226 and 326 in the distal range 238 and 338 may be at locations other than at the tip 225 and 325 of the primary electrodes 220 and 320, respectively. FIGS. 4A-F and 5A-D illustrate potential placements of one or more openings that may be used in illustrative embodiments according to the present disclosure.

Referring to FIGS. 4A and 4B, a primary electrode 410 like those described with reference to FIGS. 2A and 2B includes a single opening 412 through a tip 414 of the primary electrode 410. The primary electrode 410 and its single opening 412 in the tip 414 are configured like a Quincke needle, as understood by those ordinarily skilled in the art of using needles for delivery of fluid into a body. Vaporized conductive fluid generated using an apparatus including the primary electrode 410 may be expelled at the tip 414 of the primary electrode 410 through the single opening 412.

Referring to FIGS. 4C and 4D, a primary electrode 420 includes a single opening 422 along a side 424 of the primary electrode 420, rather than at a tip of the primary electrode 420 such as those previously described with reference to FIGS. 2A, 3A, 4A, and 4B. The primary electrode 420 and its opening 422 along the side 424 of the primary electrode 420 are configured like a Whitacre needle, as understood by those ordinarily skilled in the art of using needles for delivery of fluid into a body. Vaporized conductive fluid generated using an apparatus including the primary electrode 420 may be expelled from the side 424 of the primary electrode 420 through the single opening 422.

Referring to FIGS. 4E and 4F, a primary electrode 430 includes a single opening 432 along a side 434 of the primary electrode 430, similar to the primary electrode 420 described with reference to FIGS. 4C and 4D, although the single opening 432 in the primary electrode 430 has a different shape than the single opening 422 in the primary electrode 420 of FIGS. 4C and 4D. The primary electrode 430 and its opening 432 along the side 434 of the primary electrode 430 are configured like a Sprotte needle, as understood by those ordinarily skilled in the art of using needles for delivery of fluid into a body. Vaporized conductive fluid generated using an apparatus including the primary electrode 430 may be expelled from the side 434 of the primary electrode 430 through the single opening 432, similar to the way in which vaporized conductive fluid is expelled from the electrode 420 of FIGS. 4C and 4D.

Figure 5A:
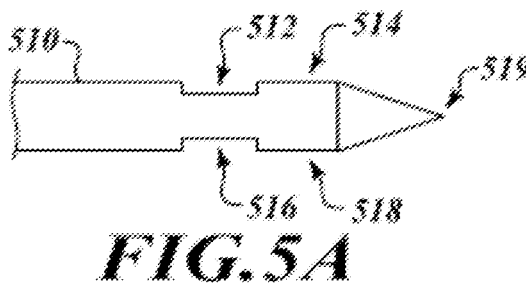
Figure 5B:
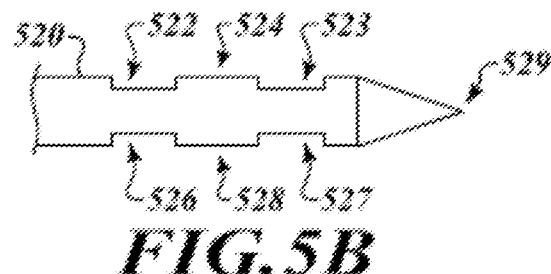
Figure 5C:
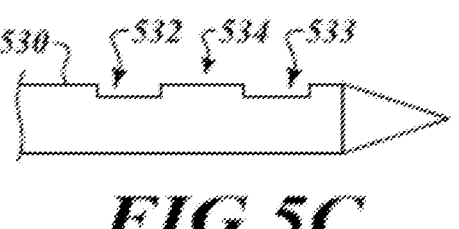
Figure 5D:
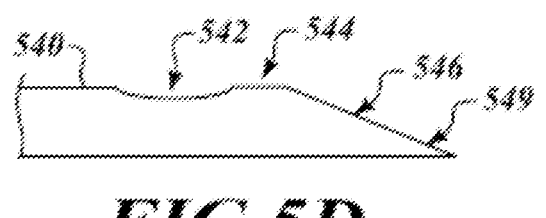

Referring to FIGS. 5A-5D, embodiments of primary electrodes may include more than one opening to the lumen so as to expel vaporized conductive fluid in more than one direction, as described with reference to the illustrative embodiments below. Referring to FIG. 5A, a primary electrode 510 includes a first opening 512 in a first side 514 and a second opening 516 in a second side 518. (The primary electrode 510 does not include an opening at a tip 519 of the primary electrode.) Referring to FIG. 5B, a primary electrode 520 includes multiple openings 522 and 523 in a first side 524 and additional openings 526 and 527 in a second side 528. (The primary electrode 520 may not include any openings at a tip 529 of the primary electrode.) Referring to FIG. 5C, a primary electrode 530 includes multiple openings 532 and 533 along a first side 534, but no additional openings. Referring to FIG. 5D, a primary electrode 540 includes a first a first opening 542 in a first side 544 and a second opening 546 in a tip 549. The examples of FIGS. 5A-5D, like those of FIGS. 4A-4F are merely illustrative; a primary electrode may be configured with any number of openings at any number of positions, as well as in any combination, to expel vaporized conductive fluid in desired directions.

Referring to FIG. 6, in some embodiments a user interface 601 is disposed at a proximal end 411 of the electrode apparatus 210 of FIG. 2. Although FIG. 6 shows the configuration of the proximal end 411 of the electrode apparatus 210, it should be understood that a proximal end of the electrode apparatus 310 of FIGS. 3A and 3B, or other electrode apparatuses according to embodiments of the present disclosure, may be similarly configured. At the proximal end 611 of the electrode apparatus, a first electrical lead 621 is electrically coupled to the primary electrode 220 and a second electrical lead 631 is electrically coupled to the secondary electrode 230. The first electrical lead 621 and the second electrical lead 631 in turn are coupled with the electrical conductor 130 (FIG. 1), which thereby electrically couples the electrode apparatus 210 with the switchable power source 114. Electrical insulation 231 covers the secondary electrode 230 at the proximal end 611 of the electrode apparatus 210, so the primary electrode 220 is electrically isolated from the secondary electrode 230 at the proximal end 611 of the electrode apparatus 210. The first electrical lead 621 and the second electrical lead 631 are similarly insulated to electrically isolate the primary electrode 220 from the secondary electrode 230. The electrical insulation of the secondary electrode 230 and the electrical leads 621 and 631 at the proximal end 411 of the electrode apparatus 210 maintain electrical isolation of the primary electrode 220 and the secondary electrode 230 even in the presence of a conductive fluid at the proximal end 611 (the introduction of which into the proximal end 611 of the electrode apparatus 210 is described below).

Once again referring to FIG. 6, the user interface 601 also includes a fluid port 651. The fluid port 651 is configured to receive a conductive fluid (not shown in FIG. 6). With reference to FIG. 1, the conductive fluid may be received from a conductive fluid source 116 via a tube 132. The conductive fluid source 116, as shown in FIG. 1, may be an electromechanical pump. However, the fluid port 651 also may receive conductive fluid via a mechanical pump, which may include a syringe, or another source of conductive fluid. The fluid port 651 is coupled with the lumen 222 of the primary electrode 220 by a tube 653. The tube 653 may be flexible or extendable so that, as the electrode apparatus 210 may be moved relative to the user interface 601 as further described below with reference to FIGS. 7 and 10A, the fluid port 651 remains coupled with the lumen 222.

Referring to FIG. 7, in various embodiments a user interface 701 helps enable a user to position the sheath 103 (FIGS. 1-3B) and the electrode apparatus 210 (FIGS. 2A and 2B) or the electrode apparatus 310 (FIGS. 3A and 3B) within a body as further described below with reference to FIGS. 8A-10B. A sheath actuator 780 is slideably received into a first end 782 of a housing 702 of the user interface 701. The sheath actuator 780 is mechanically coupled with the sheath 103 (not shown in FIG. 7) so that sliding movement of the sheath actuator 780 will result in a corresponding movement of the sheath 103 and, in turn, the distal end 105 (not shown in FIG. 7) of the sheath 103. The sheath actuator 780 includes a locking groove 781 that receives a sheath lock 783 that, in turn, is received through a sheath locking port 784 in the user interface 701.

In some embodiments and as shown in FIG. 7, the sheath lock 783 is in the form of a knurled lock screw received through a screw opening 784 in the user interface 701 and that mechanically and selectively engages the locking groove 781 in the sheath actuator 780. The sheath lock 783 may be rotated to loosen the sheath lock 783 from the locking groove 781 to enable movement of the sheath actuator 780. The sheath 103 is manipulated by sliding the sheath actuator 780 relative to the housing 702. Then, once the distal end 105 of the sheath 103 has been positioned at a desired location, the sheath lock 783 may be turned to cause the sheath lock 783 to engage the locking groove 781 in the sheath actuator 780 to lock the sheath 103 in place relative to the user interface 701. It should be appreciated that other forms of sheath actuators may be used, such as lever or a latch, to lock the sheath actuator 780 in place. It also should be understood that other forms of a sheath actuator may be fixably coupled to a housing of the user interface relative to a sheath lock joined to a port on a bronchoscope such that moving the housing results in moving the sheath, as is further described below with reference to FIGS. 8A and 9A. Accordingly, it will be appreciated that embodiments of the present disclosure are not limited to use of any form of sheath actuator system.

Still referring to FIG. 7, in various embodiments an electrode actuator 790 may be embodied in the form of a slidable lever that is fixably joined to the electrode apparatus 210 at or near a proximal end 611 (FIG. 6). The electrode actuator 790 extends through an actuator groove 791 in the housing 702 of the user apparatus to engage the electrode apparatus 210 at or near the proximal end 611 of the electrode apparatus 210. In some embodiments, the electrode actuator 790 may be spring-loaded or otherwise configured to engage the actuator groove 791 or another part of the housing 702 to hold the electrode actuator 790—and thus the electrode apparatus 210—in place once the electrode apparatus 210 has been slidably moved to a desired location.

As shown in FIG. 7, in various embodiments a source of conductive fluid is received at a fluid port 751 in a side of the housing 702 of the user interface 701, similar to the fluid port 651 described with reference to FIG. 6. A fluid source 753, which may represent an end of the tube 132 coupled to the conductive fluid source 116 (FIG. 1), or may represent a tube from another fluid pump, a lumen of a syringe, or another source of conductive fluid. As described with reference to FIG. 6, in some embodiments the fluid port 751 enables a conductive fluid (not shown) to be supplied to the lumen 222 of the primary electrode 220.

Referring to FIGS. 8A and 8B, an initial configuration of an apparatus 800 includes another illustrative user interface 805 received at a port 148 of an electrosurgical apparatus 118, such as a bronchoscope or another minimally invasive device used for performing diagnostic or therapeutic tasks by extending a sheath or catheter into a body as shown in FIG. 1. In the apparatus 800 of FIG. 8A, the user interface 805 includes a sheath actuator 880 and a sheath lock 883 configured to move the sheath 103 (FIG. 8B) to a desired location to position a distal end 105 of the sheath 103 relative to a region 803 adjacent a reference point 801. The region 803 may represent or may include a lesion or other targeted object to be ablated or otherwise engaged by embodiments of the disclosure.

The user interface 805 is similar in operation, but not necessarily identical to, the user interface 701 as was previously described with reference to FIG. 7. As was previously described with reference to FIG. 7, in some embodiments, the sheath actuator 880 may be a slidable sleeve. In contrast to the embodiment of FIG. 7, however, the slidable sleeve that comprises the sheath actuator 880 may be fixably coupled to the housing 802 of the user interface 805 and slidably received within a collar 882 that is secured to the port 148 of the electrosurgical apparatus 118. The sheath actuator 880 thus may be manipulated by moving the housing 802 and the fixably coupled sheath actuator 880 relative to the collar 882 (instead of by moving the sheath actuator 770 relative to the housing 702, as in the embodiment of FIG. 7). The sheath actuator 880 then may be secured at a desirable location at the collar 882 by a sheath lock 883 integrated with the collar 882. The sheath lock 883 may be a spring-loaded locking pin, a thumbscrew, or another mechanism configured to mechanically engage the sheath actuator 880 to secure the sheath actuator 880—and, in turn, the sheath 103 (FIGS. 2A and 3A)—in place at a desired location.

As was previously described with reference to FIG. 7, in various embodiments, the user interface 805 is mechanically coupled with the electrode apparatus 210, which is slidably received within the sheath 103. In an initial deployment configuration, the electrode apparatus 210, including the primary electrode 220, the secondary electrode 230, and the separator 240, are received within the distal end 105 of the sheath 103, with the distal end 224 of the primary electrode 220 at a position short of the distal end 105 of the sheath 103. As also described with reference to FIG. 7, an electrode actuator 890 in an actuator groove 891 is in a retracted position corresponding with the electrode apparatus 210 being positioned within the distal end 105 of the sheath. The electrode apparatus 210 is configured to move in concert move in concert with the sheath 103 as the sheath 103 is moved until the electrode actuator 890 is engaged.

Referring to FIGS. 9A and 9B, in a next configuration of the apparatus 900, manipulation of the sheath actuator 880 illustrates an example of how the sheath 103 may be unlocked and moved into position. In the configuration shown in FIGS. 9A and 9B, the sheath actuator 980 has been manipulated to move sheath 103 a distance 919 toward to the reference point 801. To move the sheath 103 as shown in FIG. 9B, the sheath lock 883 is manipulated to enable movement of the sheath actuator 880 within the collar 882, then the housing 810 is moved the distance 919 toward the collar 882 to move the sheath 103 the corresponding distance 919 toward the reference point 801. Once the distal end 105 of the sheath 103 has reached the desired location, the sheath actuator 880 may be locked in position at the collar 882 by manipulating the sheath lock 883. Because the electrode actuator 890 has not been moved to move the electrode apparatus 210 relative to the sheath 103, the electrode apparatus 210 remains contained within the distal end 105 of the sheath, with the distal end 224 of the primary electrode 220 positioned short of the distal end 105 of the sheath 103, as shown in FIG. 9B.

Referring to FIGS. 10A and 10B, in a further configuration of the apparatus 1000, once the distal end 105 of the sheath 103 has been positioned in a desired location relative to the reference point 801, the electrode apparatus 210 is moved into place. By sliding the electrode actuator 890 through a distance 1019, the distal end of 224 of the primary electrode 220—and the electrode apparatus 210 as a whole—is advanced a corresponding distance 1019 toward and/or to the reference point 801. As shown in FIG. 10B, because the primary electrode 220 is needle-shaped at its distal end 224 as previously described with reference to FIGS. 2A, 3A, 4A-4F, and 5A-5D, the primary electrode 220 may pierce tissue at or near the reference point 801, thereby enabling the electrode apparatus 210 to be inserted through and/or into the region 803 of tissue or lesion to be treated. With the electrode apparatus 210 so positioned, the distal opening 226 in the lumen 222 is presented within, at, or adjacent to the lesion or other tissues to be treated in the region 803 adjacent the reference point 801 with vaporized conductive fluid as further described below with reference to FIGS. 12 and 16.

Referring to FIG. 11, in some embodiments, after the electrode apparatus 210 is positioned at a desired location relative to the reference point 801 in the region 803, a flow of conductive fluid 1160 is supplied to the electrode apparatus 210. The conductive fluid may be a saline solution or another conductive fluid. As previously described with reference to FIGS. 1 and 6, for example, a conductive fluid source, such as an electromechanical pump 116 (FIG. 1), a mechanical pump, a syringe, or another conductive fluid source is coupled with the electrode apparatus at its proximal end. The conductive fluid source is directed to cause a flow of conductive fluid 1160 to pass into and through the lumen 222 of the primary electrode 220.

The flow of conductive fluid 1160 results in a quantity of conductive fluid 1161 flowing into the distal range 238 through fluid openings 242 or 342 (not shown in FIG. 9) in the one or more separators 240 or 340, respectively, as described with reference to FIGS. 2B and 3B. The quantity of conductive fluid 1161 flowing into the distal range 238 will be in electrical contact with the primary electrode 220 and the secondary electrode 230 adjacent the distal ends 224 and 234 of the primary electrode 220 and the secondary electrode 230, respectively. As previously described, openings 236 formed in the electrical insulation 231 of the secondary electrode 230 permit the quantity of conductive fluid 1161 to be in electrical contact with the secondary electrode 230 in the distal range 238 near the distal ends 224 and 234 of the primary electrode 220 and the secondary electrode 230, respectively, even though the electrical insulation 231 electrically isolates the secondary electrode 230 from the primary electrode 220 at other points.

Referring to FIG. 12, after the quantity of conductive fluid 1161 (FIG. 11) has been received in the distal range 238, a switchable power source, such as the switchable power source 114 (FIG. 1), in electrical communication with the primary electrode 220 and the secondary electrode 230, is activated. The primary electrode 220 and the secondary electrode 230, as previously described, are electrically connected to separate poles of the switchable power source. When the switchable power source is activated, the electrical power applied between the primary electrode 220 and the secondary electrode 230 in contact with the quantity of conductive fluid 1161 (FIG. 11) in the distal range 238 causes the quantity of conductive fluid 1161 to be vaporized to generate a fluid vapor 1205 that is expelled through the distal opening 226 in the lumen 222 of the primary electrode 220 to ablate or otherwise affect tissue in the region 803 adjacent the reference point 801. In this manner, for example, if the region 803 represents a lesion, the fluid vapor 1205 may therefore ablate the lesion or other tissue, thereby enabling treatment of the lesion or other tissue by insertion of the electrode apparatus 210 into the body without more invasive surgery.

Referring again to FIG. 11, it has been illustrated how the quantity of conductive fluid 1161 may be supplied to the distal range 238 for vaporization internally through the electrode apparatus 210 once the electrode apparatus 210 is situated at a desired location at or near the reference point. However, as shown in FIGS. 13-16, conductive fluid also may be supplied to the distal range 238 via a passage external to the electrode apparatus 210 or may be supplied before the electrode apparatus is inserted into the region 803 adjacent the reference point 801, as further described below with reference to FIGS. 13-16. FIGS. 13-16 depict an electrode apparatus 1310 that corresponds in most respects to the electrode apparatus 210 previously described with reference to FIGS. 2A, 2B, 11, and 12. Accordingly, except for any changed structures, the same reference numbers will be used in describing the electrode apparatus 1310 as were used for the electrode apparatus 210.

Figures 13, 14:
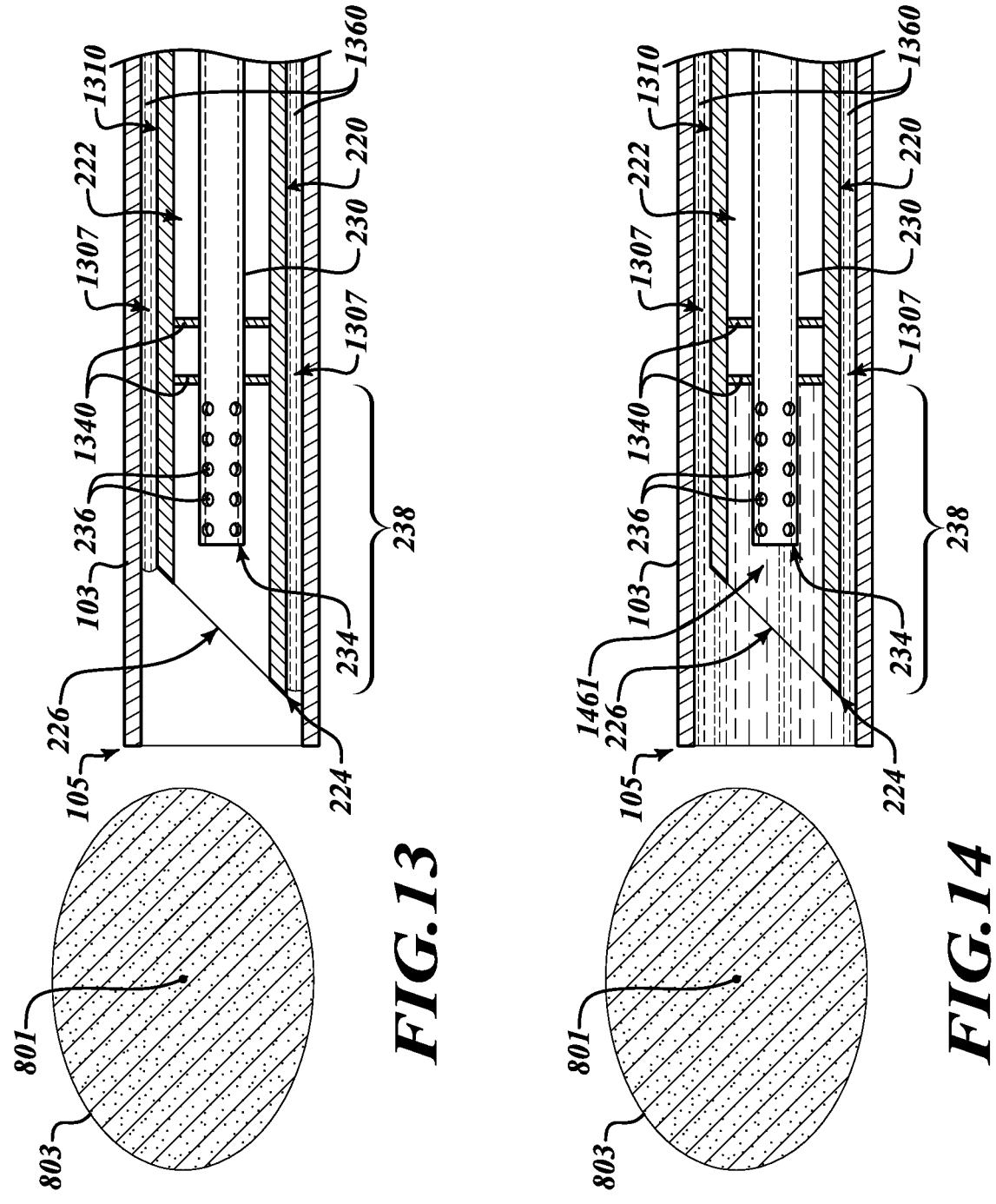

Referring to FIG. 13, in various embodiments the electrode apparatus 1310 may receive a flow of conductive fluid 1360 supplied through a fluid tube other than through the lumen 222 of the primary electrode 220 as previously described. For example, the conductive fluid 1360 may be conveyed to the distal range 238 using a fluid tube. As shown in FIGS. 13-16, the fluid tube may be the sheath 103 through which the electrode apparatus extends or a separate tube included in the electrode apparatus 1310. The conductive fluid 1360 may flow within a gap 1307 between the sheath 103 and the electrode apparatus 1310 The conductive fluid 1360 is provided by a pump, such as an electromechanical pump, a syringe, another form of mechanical pump, etc., as previously described, may be coupled to a proximal end (not shown) of the sheath 103 to pass the conductive fluid 1360 to the distal range. As previously mentioned, a fluid tube that is separate from the sheath 103 also may be used to supply the conductive fluid 1360 to the distal range 238. It should be noted that, if the conductive fluid 1360 is supplied other than through the lumen 222 of the primary electrode 220, the separators 1340 may be circumferentially uniform and would not include a fluid opening 242 as previously described with reference to FIGS. 2B and 3B.

Referring to FIG. 14, in various embodiments the conductive fluid 1360 (supplied via the sheath 103 acting as a fluid tube) may flow through the gap 1307 between the sheath 103 and the electrode apparatus 1310 to the distal range to provide a quantity of conductive fluid 1461 to the distal range 238. As shown in FIG. 14, the quantity of conductive fluid 1461 is supplied to the distal range 238 before the electrode apparatus 1110 is extended to or into the region 803 adjacent the reference point 801. However, it should be understood that, if a fluid tube coupled to the electrode apparatus 1310 other than the sheath 103 from which the electrode apparatus 1310 extends into the region 803 were to be used, the quantity of conductive fluid 1461 may also be supplied to the distal region 238 after the electrode apparatus 1310 has been inserted to or into the region 803. The quantity of conductive fluid 1461 may be received into the distal range 238 via the distal opening 226 in the lumen 222 of the primary electrode 220.

Figures 15, 16:
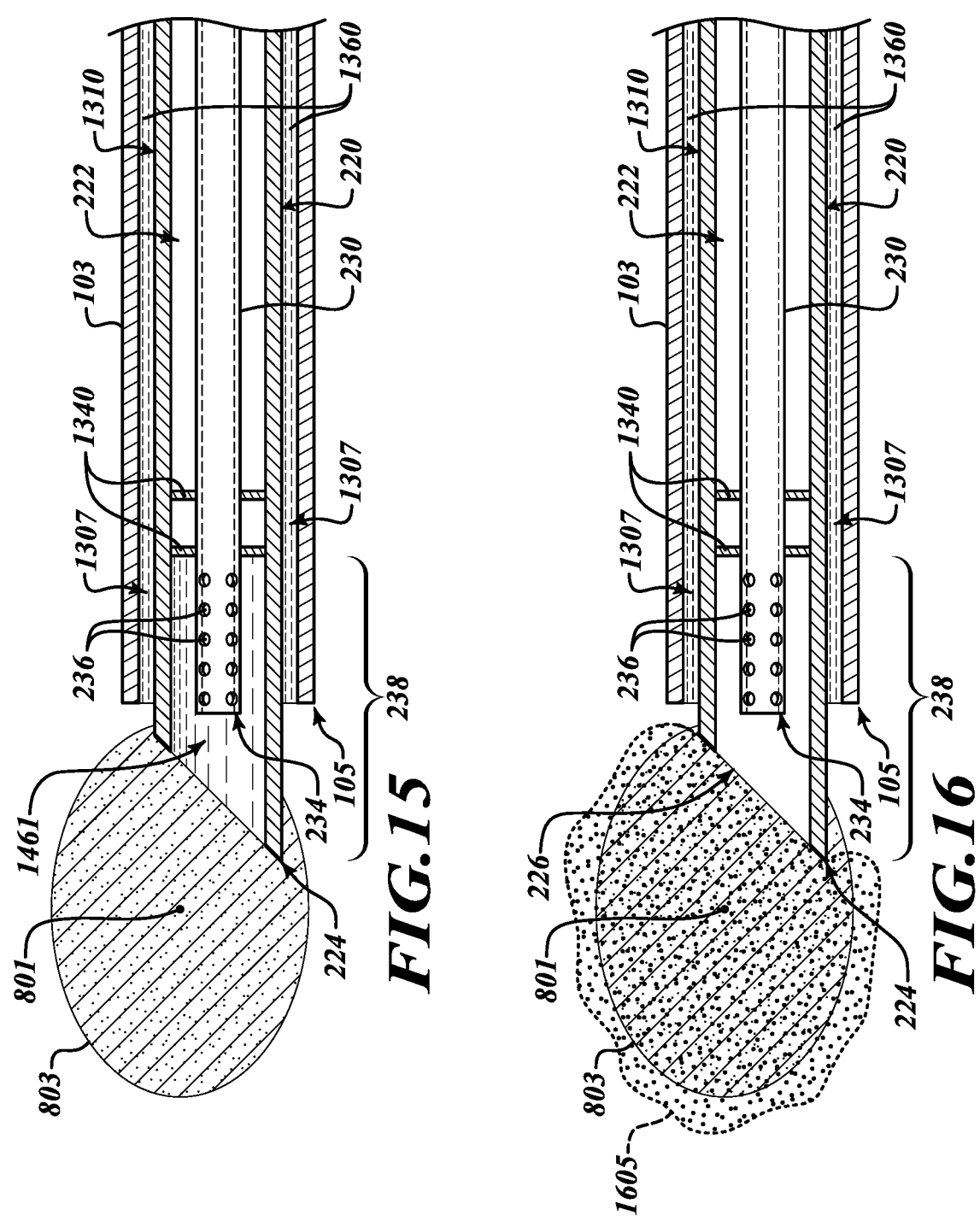

Referring to FIG. 15, with the quantity of conductive fluid 1461 within the distal range 238, the electrode apparatus 1110 is extended beyond the distal end of the sheath 103 to or into the region 803 adjacent the reference point 801. Extending the electrode apparatus 1310 thus positions the distal opening 226 in the lumen 222 of the primary electrode 220 from which vaporized conductive fluid may be used to treat a lesion or other tissue. Referring to FIG. 16, as described with reference to FIG. 12, electrical power is selectively applied to the primary electrode 220 and the secondary electrode 230 to cause the quantity of conductive fluid 1461 to vaporized and expelled through the distal opening 226 in the lumen 222 of the primary electrode 220. A fluid vapor 1605 generated and expelled via the distal opening 226 in the primary electrode may therefore ablate or otherwise affect or treats tissue in the region 803 at or near the reference point 801.

In the examples of FIGS. 11-16, conductive fluid is vaporized and expelled through a single, distal opening 226 in the primary electrode 210. However, as previously described with reference to FIGS. 4A-4F and 5A-5D, other configurations of the primary electrode may include one or more openings formed in the distal range of the primary electrode at a tip of the primary electrode and/or along one or more sides of the primary electrode. Accordingly, just as the vaporized conductive fluid may be expelled from a single distal opening in the primary electrode, the vaporized conductive fluid may be expelled from openings along a side of the primary electrode or from multiple openings along one or more sides and/or the tip of the primary electrode, as described with reference to FIGS. 17-19.

Referring to FIG. 17, a primary electrode 1720 includes a single opening 1722 along a side 1724 of the primary electrode 1720 through which a quantity of vaporized conductive fluid 1705 is expelled. Referring to FIG. 18, a primary electrode 1820 includes openings 1822 and 1823 along different sides 1824 and 1825 through which quantities of vaporized conductive fluid 1805 and 1807 are expelled, respectively. Referring to FIG. 19, a primary electrode 1920 includes openings 1922 and 1923 along different sides 1924 and 1925 through which quantities of vaporized conductive fluid 1905 and 1907 are expelled, respectively, and a distal opening 1927 in a tip 1928 of the primary electrode 1920 through which another quantity of vaporized conductive fluid 1929 is expelled. Again, as described with reference to FIGS. 4A-4F and 5A-5D, embodiments of the present disclosure are not limited to a particular number or placements of openings in the primary electrode through which vaporized conductive fluid may be expelled.

Referring to FIG. 20 an illustrative method 2000 of operating an electrode apparatus is provided. The method 2000 starts at a block 2005. At a block 2010, an electrode apparatus is extended to a location adjacent a reference point. The electrode apparatus includes a primary electrode defining a lumen therein and defines at least one opening to the lumen within a distal range adjacent a first distal end of the primary electrode and a secondary electrode extending through the lumen to a second distal end within the distal range. The secondary electrode is electrically insulated from the primary electrode except within at least a portion of the distal range, as previously described. The configuration of the electrode apparatus, a user interface configured to control positions of the sheath and the electrode apparatus, other supporting devices, and the operation thereof is previously described with reference to FIGS. 2A-19.

At a block 2020, a conductive fluid is supplied to the distal range of the electrode apparatus. As previously described with reference to FIG. 11, the conductive fluid may be supplied via the lumen in the primary electrode, passing through fluid openings in one or more separators. Alternatively, as described with reference to FIGS. 13-14, the conductive fluid may be supplied via a separate fluid tube, such as the sheath. The conductive fluid may be supplied to the distal range of the electrode apparatus before or after the electrode apparatus is extended to the reference point, as previously described with reference to FIGS. 11-12 and 13-14.

At a block 2030, electrical power is selectively applied to the primary electrode and the secondary electrode. The electrical power may be selectively applied to proximal ends of the electrodes, as previously described with reference to FIG. 6. Coupling the electrical power to the primary electrode and the secondary electrode causes the conductive fluid to be vaporized at the distal range of the electrode apparatus. The vaporization of the conductive fluid thus may ablate or otherwise affect tissue at the reference point. The method 2000 ends at a block 2035.

It will be appreciated that the present descriptions of the electrode apparatuses, systems, and methods described herein as being used for treatment of vaporizing tissue may be used for treating lesions or other tissues in the lung using a bronchoscope as described with reference to FIG. 1 are not limiting, and that these embodiments may be used for treating tissue via other instruments and in others areas of interest on a patient, including gastric, endoscopic, or other suitable locations. Similarly, a bronchoscope is not necessary, and other suitable devices capable of accommodating the embodiments described herein may also be used, including without limitation various endoscopes or laparoscopic cannulas.

It will also be appreciated that the detailed description set forth above is merely illustrative in nature and variations that do not depart from the gist and/or spirit of the claimed subject matter are intended to be within the scope of the claims. Such variations are not to be regarded as a departure from the spirit and scope of the claimed subject matter.

What is claimed is:

1. An apparatus for bipolar ablation, the apparatus comprising:

a pair of coaxially-arranged ablation electrodes adapted for bipolar ablation and configured to be inserted through a bronchoscope insertable through an orifice of a body and into a lung of the body, the pair of coaxially-arranged ablation electrodes including:

a primary electrode having a first distal end positionable adjacent to a lesion within the lung and having a first proximal end selectively couplable with a first pole of a power source, the primary electrode defining a lumen therein extending from the first proximal end to the first distal end and configured to convey a saline solution from adjacent the first proximal end to the first distal end, the first distal end defining at least one opening to the lumen adjacent the first distal end; and a secondary electrode extending through the lumen of the primary electrode from the first proximal end to the first distal end, the secondary electrode having a second distal end extending through a separator into a distal range adjacent the first distal end and a second proximal end selectively couplable with a second pole of the power source, the secondary electrode being electrically insulated from the primary electrode except within the distal range, wherein the saline solution conveyed through the lumen and around the secondary electrode is receivable within the first distal end so as to be in electrical contact with the primary electrode and the secondary electrode, the saline solution being vaporizable within the first distal end between the primary electrode and the second distal end of the secondary electrode responsive to application of power across the first pole and the second pole of the power source to generate steam expellable through the at least one opening to apply the steam to ablate the lesion within the lung wherein the secondary electrode extending through the lumen within the primary electrode forms an annular lumen coupled to a source of saline solution to deliver the saline solution into the distal range, wherein the separator forms an annular ring within the annular lumen of the primary electrode.

2. The apparatus of claim 1, wherein the at least one opening defined by the primary electrode to the lumen within the distal range includes at least one of:

a distal opening at a tip of the primary electrode;

at least one lateral opening at a side of the primary electrode.

3. The apparatus of claim 1, wherein the first distal end of the primary electrode is configured to pierce tissue.

4. The apparatus of claim 1, further comprising a second separator positioned proximate of the separator adjacent to the distal range configured to separate the secondary electrode from the primary electrode within the lumen.

5. The apparatus of claim 1, wherein the lumen is fluidly couplable with a saline solution source to convey the saline solution from adjacent the first proximal end of the primary electrode to the distal range.

6. The apparatus of claim 1, wherein the separator defines a most proximal position of the distal range.

7. The apparatus of claim 1, wherein the separator is configured to maintain electrical isolation between the primary electrode and the secondary electrode within the distal range prior to introduction of the saline solution.

8. The apparatus of claim 1, wherein the separator includes a fluid opening to allow the saline solution to enter the distal range.

9. A system for bipolar ablation including a pair of coaxially-arranged electrodes within a sheath, the system comprising:

a power source configured to selectively power between a first pole and a second pole;

a source of saline solution;

the pair of coaxially-arranged electrodes adapted for bipolar ablation and insertable into the sheath configured to be inserted through a bronchoscope insertable through an orifice of a body of a patient and into a lung of the body, the pair of coaxially-arranged electrodes including:

a primary electrode having a first distal end positionable adjacent to a lesion within the lung and having a first proximal end selectively couplable with the first pole of a power source, the primary electrode defining a lumen therein extending from the first proximal end to the first distal end and configured to convey the saline solution from adjacent the first proximal end to the first distal end, the first distal end defining at least one opening to the lumen adjacent the first distal end; and a secondary electrode extending through the lumen of the primary electrode from the first proximal end to the first distal end, the secondary electrode having a second distal end extending through an annular ring into a distal range adjacent the first distal end and a second proximal end selectively couplable with the second pole of the power source, the secondary electrode being electrically insulated from the primary electrode except within the distal range, wherein the saline solution conveyed through the lumen and around the secondary electrode is receivable within the first distal end so as to be in electrical contact with the primary electrode and the secondary electrode, the saline solution being vaporizable within the first distal end between the primary electrode and the second distal end of the secondary electrode responsive to application of power across the first pole and the second pole of the power source to generate steam expellable through the at least one opening to apply the steam to ablate the lesion within the lung; and a user interface configured to control extension of the primary electrode and the secondary electrode through the bronchoscope within the body of the patient, wherein the secondary electrode extending through the lumen within the primary electrode forms an annular lumen coupled to the source to deliver the saline solution into the distal range, wherein the annular ring is disposed within the annular lumen of the primary electrode.

10. The system of claim 9, wherein the at least one opening defined by the primary electrode to the lumen within the distal range includes at least one of:

a distal opening at a tip of the primary electrode;

at least one lateral opening at a side of the primary electrode.

11. The system of claim 9, wherein the first distal end of the primary electrode is configured to pierce tissue.

12. The system of claim 9, wherein the annular ring defines a most proximal position of the distal range.

13. The system of claim 9, wherein the annular ring is configured to maintain electrical isolation between the primary electrode and the secondary electrode within the distal range prior to introduction of the saline solution.

14. The system of claim 9, wherein the annular ring includes a fluid opening to allow the saline solution to enter the distal range.

* * * * *